United States Patent [19]

Buhr

[11] Patent Number: 4,696,888
[45] Date of Patent: Sep. 29, 1987

[54] LIGHT-SENSITIVE COMPOUNDS POSSESSING TRICHLOROMETHYL GROUPS, A PROCESS FOR THEIR PRODUCTION AND LIGHT-SENSITIVE MIXTURES CONTAINING THESE COMPOUNDS

[75] Inventor: Gerhard Buhr, Koenigstein, Fed. Rep. of Germany

[73] Assignee: Hoechst Aktiengesellschaft, Frankfurt am Main, Fed. Rep. of Germany

[21] Appl. No.: 890,537

[22] Filed: Jul. 30, 1986

Related U.S. Application Data

[62] Division of Ser. No. 660,098, Oct. 12, 1984, Pat. No. 4,619,998.

[30] Foreign Application Priority Data

Oct. 12, 1983 [DE] Fed. Rep. of Germany ....... 3337024

[51] Int. Cl.[4] .................... G03C 1/495; G03C 1/70; G02B 5/23; F21V 9/04
[52] U.S. Cl. .................... 430/270; 430/281; 430/280; 430/292; 430/343; 430/344; 430/916; 430/920; 430/925; 430/945; 522/63; 522/16; 522/26; 522/14; 252/586; 252/589
[58] Field of Search .................... 522/63, 16, 26, 14; 430/281, 270, 280, 292, 343, 344, 916, 920, 925, 945; 252/586, 589

[56] References Cited

U.S. PATENT DOCUMENTS 3,954,475  5/1976  Bonham et al. .................... 96/67
3,987,037 10/1976  Bonham et al. .................... 260/240 D
4,189,323  2/1980  Buhr .................... 430/281
4,239,850 12/1980  Kita et al. .................... 430/281
4,294,909 10/1981  Lee .................... 522/63 X
4,476,215 10/1984  Kausch .................... 522/63 X
4,506,003  3/1985  Ruckert et al. .................... 522/63 X

FOREIGN PATENT DOCUMENTS 81-02261  8/1981  PCT Int'l Appl. .

Primary Examiner—John E. Kittle
Assistant Examiner—Cynthia Hamilton
Attorney, Agent, or Firm—Schwartz, Jeffery, Schwaab, Mack, Blumenthal & Evans

[57] ABSTRACT

Light-sensitive compounds are described which have the formula

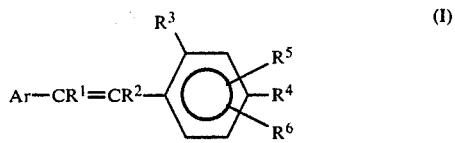

wherein $R^1$ and $R^2$ denote H or alkyl, $R^3$ and $R^4$ denote H or 4,6-bis-trichloromethyl-s-triazin-2-yl, $R^5$ and $R^6$ denote H or halogen, alkyl, alkenyl or alkoxy, and Ar denotes a mononuclear to trinuclear aromatic group.

These compounds are suitable as photoinitiators for free-radical polymerizations or as photolytic acid donors for acid-cleavable compounds, and for cross-linking and color formation reactions. They are distinguished by a high sensitivity in various spectral ranges.

9 Claims, No Drawings

LIGHT-SENSITIVE COMPOUNDS POSSESSING TRICHLOROMETHYL GROUPS, A PROCESS FOR THEIR PRODUCTION AND LIGHT-SENSITIVE MIXTURES CONTAINING THESE COMPOUNDS

This is a division of application Ser. No. 660,098, filed Oct. 12, 1984, U.S. Pat. No. 4,619,998.

BACKGROUND OF THE INVENTION

The present invention relates to bis-4,6-trichloromethyl-s-triazines which at their 2-position are substituted by an aromatic group, and to a light-sensitive mixture containing these compounds.

Triazine compounds of the above-mentioned type are known to be initiators for a number of photochemical reactions. They are employed, on the one hand, to produce free radicals, formed by the action of actinic radiation, for starting polymerization reactions or color changes and, on the other hand, to initiate secondary reactions caused by the acid freed by the action of the actinic radiation.

German Offenlegungsschrift No. 22 43 621 describes styryl-substituted trichloromethyl-s-triazines which exhibit a number of advantageous properties. However, a disadvantage is presented by their relatively complicated manufacture.

German Offenlegungsschrift No. 27 18 259 discloses 2-aryl-4,6-bis-trichloromethyl-s-triazine compounds with polynuclear aryl groups, which compounds have comparably good properties, in particular, a high sensitivity to light, and which can be produced by simple methods. In general, however, they show this high sensitivity in one spectral range only. As a consequence, they cannot be processed into light-sensitive materials which display the same high sensitivity to various light sources, for example, argon ion lasers and gallium-doped mercury vapor lamps, respectively.

German Offenlegungsschrift No. 28 51 641 discloses combining photopolymerization initiators of diverse chemical constitution with photopolymerization initiators containing trichloro-methyl groups, in order to achieve various desired properties in one single mixture.

SUMMARY OF THE INVENTION

It is an object of the present invention to provide novel compounds which can be used as photoinitiators and which can be synthesized using simple methods, but which display a sensitivity, both to the UV radiation of an argon ion laser and to the radiation of a gallium-doped mercury vapor high pressure lamp in the visible spectral range, that is at least comparable to that of the photoinitiators which, in the aforementioned respective spectral ranges, are particularly sensitive.

It is another object of the present invention to provide a light-sensitive mixture that can be used to advantage as constituents in photopolymerizable and other kinds of photosensitive layers.

It is yet another object of the present invention to provide a simple process for producing novel triazine compounds which possess useful photosensitivity properties.

In accomplishing the foregoing objects, there has been provided, in accordance with the present invention, a class of novel light-sensitive compounds having the formula

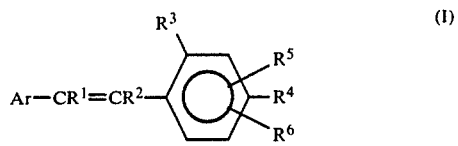

wherein $R^1$ and $R^2$ each denotes a hydrogen atom or an alkyl group, $R^3$ and $R^4$ are different from one another and each denotes a hydrogen atom or a 4,6-bistrichloromethyl-s-triazin-2-yl group $R^5$ and $R^6$ are identical or different and each denotes a hydrogen atom, a halogen atom, or substituted or unsubstituted alkyl, alkenyl or alkoxy groups, and Ar denotes a substituted or unsubstituted mononuclear to trinuclear aromatic group.

In accordance with another aspect of the present invention, there has been provided a light-sensitive mixture which contains a bis-trichloromethyl-s-triazine (a) and a compound (b) which is capable of reacting with the photoreaction product of triazine (a) in such a way that a product is formed, the light absorption or solubility in developer of which is different from that of compound (b). The mixture of the present invention is characterized in that triazine (a) is a compound of the above-defined formula I.

In accordance with still another aspect of the present invention, there has been provided a process for producing the aforementioned triazines of formula I, comprising the step of co-trimerizing, in the presence of hydrogen halide and at least one Friedel-Crafts catalyst, 1 mole of a compound having the formula

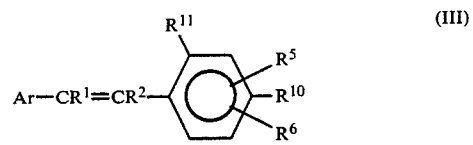

wherein $R^{10}$ and $R^{11}$ are different from one another and each denotes a hydrogen atom or a CN-group, and Ar, $R^1$, $R^2$ $R^5$ and $R^6$ are as defined above, with about 2 to about 8 moles of trichloroacetonitrile.

Other objects, features, and advantages of the present invention will become apparent from the following detailed description. It should be understood, however, that the detailed description and specific examples, while indicating preferred embodiments of the invention, are given by way of illustration only, since various changes and modifications within the spirit and scope of the invention will become apparent to those skilled in the art from this detailed description.

DETAILED DESCRIPTION OF PREFERRED EMBODIMENTS

Under the action of actinic radiation, the compounds according to the invention form free radicals which are capable of initiating chemical reactions, in particular, free-radical initiated polymerizations. When being irradiated, they also form hydrogen halide, by which acid-catalyzed reactions, such as, for example, splitting of acetal bonds, or salt formation, or color changes of indicator dyestuffs, can be initiated.

For the purpose of this description, the term "actinic radiation" will denote any radiation whose energy at least corresponds to that of short-wave visible light. Long-wave UV radiation is particularly suitable, but electron, x-ray and laser beams, among others, can also be used.

The symbols in the formula I above preferably have the following meanings:

$R^1$ and $R^2$ each denotes a hydrogen atom or a methyl group, particularly a hydrogen atom;

$R^5$ denotes a hydrogen atom;

$R^6$ denotes a hydrogen atom, chlorine atom, a bromine atom, an alkyl group having 1 to 3 carbon atoms, or a methoxy group; and Ar denotes a phenyl group of the formula

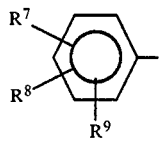
(II)

wherein $R^7$ to $R^9$ are identical or different and each denotes a hydrogen atom; a halogen atom, preferably selected from fluorine, chlorine and bromine; an alkyl group which is unsubstituted or is substituted by halogen atoms, preferably chlorine or bromine, or by aryl or aryloxy groups, and in which individual methylene groups can be replaced by oxygen or sulphur atoms, whereby any two of said groups $R^7$ through $R^9$ can be linked to form a 5-or 6-membered ring; a cycloalkyl group; an alkenyl group; an aryl group or an aryloxy group, the maximum total number of carbon atoms contained in said groups $R^7$ through $R^9$ being 12.

Ar can furthermore denote a naphthyl, an acenapthyl, dihydronaphthyl, a tetrahydronaphthyl, an indanyl, an anthryl, a phenanthryl, a fluorenyl or a tetrahydrophenanthryl group which optionally is substituted by halogen atoms, preferably chorine or bromine atoms, by alkyl groups having 1 to 3 carbon atoms, by alkoxy groups having 1 to 4 carbon atoms, or by alkoxyalkyl groups having 3 to 6 carbon atoms.

Particular preference is given to compounds of formula I
wherein
$R^1$, $R^2$, $R^3$,
$R^5$ and $R^6$ each denotes a hydrogen atom, and
Ar corresponds to the above-defined formula II, wherein
$R^7$ to $R^9$ are identical or different and each denotes a hydrogen atom, a fluorine atom, a chlorine atom, a bromine atom, an alkyl group, an alkoxy group or an alkoxy-alkyl group; or
$R^7$ denotes a hydrogen atom and
$R^8$ and $R^9$ together denote a dioxymethylene group.

A compound which is very particularly preferred is 2-(4-styryl-phenyl)-4,6-bis-trichloromethyl-s-triazine.

Specific examples of particularly preferred compounds forming the Ar groups are: phenyl; 2-, 3- or 4-fluorophenyl; 2-, 3- or 4-chlorophenyl; 2-, 3- or 4-bromophenyl; 2-, 3- or 4-methyl, -ethyl, -propyl, -butyl, -isobutyl, -hexyl, -nonyl or -dodecyl phenyl; 2-, 3- or 4-methoxy, -ethoxy, -isopropoxy, -butoxy, -pentoxy, -octyloxy or -decyloxy phenyl; 2,4-dichloro or -dibromophenyl; 3,4-dichloro- or -dibromophenyl; 2,6-dichlorophenyl; 3-bromo-4-fluorophenyl; 2,3-, 2,4-, 2,5-, 3,4- or 3,5-dimethoxy-, -diethoxy-, -dibutoxy- or -dihexoxy phenyl; 2-ethoxy-5-methoxy phenyl; 3-chloro-4-methyl phenyl; 2,4-dimethyl phenyl; 2-, 3- or 4-methoxyethyl, -ethoxyethyl or -butoxyethyl phenyl; 2,4,6-trimethyl phenyl; 3,4,5-trimethoxy or -triethoxy phenyl; 2,3-dioxymethylene phenyl; and 3,4-dioxymethylene phenyl.

The simplest and preferred way of producing the aryl-bis-trichloromethyl-s-triazines according to the present invention is by co-trimerizing about 1 mole of aryl carboxylic acid nitrile having the formula

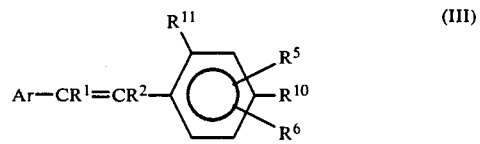
(III)

wherein $R^{10}$ and $R^{11}$ are different from one another and each denotes a hydrogen atom or a CN group, and Ar, $R^1$, $R^2$, $R^5$ and $R^6$ have the same meaning as defined for formula (I) above, with about 2–8 moles of trichloroacetonitrile in the presence of hydrogen halide, preferably hydrogen chloride, and at least one Friedel-Crafts catalyst, such as Al $Cl_3$, Al $Br_3$, $TiCl_4$ and borotrifluoride etherate. A somewhat similar synthesis is described in the *Bull. Chem. Soc. Jap.* 42:2924 (1969).

Other ways of performing the synthesis include, for example, reacting aryl amidines with polychloro-3-azapent-3-ene in accordance with the method disclosed in *Angew. Chemie* 78:982 (1966), and reacting carboxylic acid chlorides or carboxylic acid anhydrides with N-(iminoacyl)-trichloro-acetamidines. 2-aryl-4-methyl-6-trichloromethyl-s-triazines can also be easily prepared by the latter reaction, as is described in British Patent Specification No. 912,112.

The nitriles employed for co-trimerization in accordance with the present invention can be synthesized in a particularly simple way by a Horner-Wittig reaction (see METHODEN DER ORGAN. CHEMIE ("Methods of Organic Chemistry"), vol. 5/1b (Houben-Weyl 1972) (hereinafter "Houben-Weyl"), at pages 396–401 and 895–899) which follows the scheme

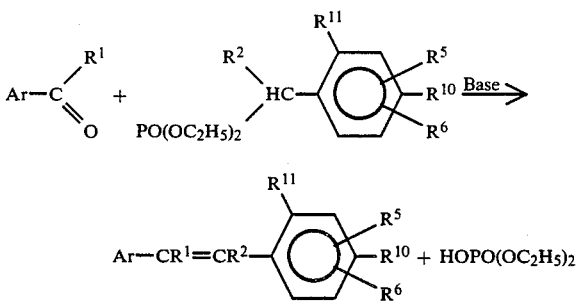

wherein $R^{10}$ or $R^{11}$ denotes the nitrile group and all other groups have the same meaning as in formula I above. The aralkylphosphonic acid diethyl ester used in the above reaction scheme is obtained by reacting the corresponding α-halogenoalkyl aromatic compound with triethyl phosphite.

The nitriles used for co-trimerization in accordance with the present invention can also be prepared by other methods which are described in the literature, for example, by exchange reactions or from the corresponding carboxylic acids or carboxylic acid derivatives. Houben-Weyl discloses a great number of syntheses for producing substituted stilbenes.

The novel compounds according to the invention are suitable as photoinitiators for photopolymerizable layers which contain, as essential constituents, monomers, binders and initiators. Photopolymerizable monomers which can be employed for this purpose are known and are described, for example, in U.S. Pat. Nos. 2,760,863 and No. 3,030,023.

Preferred examples of suitable monomers are acrylic and methacrylic acid esters of polyhydric alcohols, such as diglycerol diacrylate, polyethylene glycol dimethacrylate, acrylates and methacrylates of trimethylol ethane, trimethylol propane and pentaerythritol, and of polyhydric alicyclic alcohols. Reaction products of diisocyanates with partial esters of polyhydric alcohols are also used advantageously. Monomers of this kind are described in German Offenlegungsschriften Nos. 20 64 079, 23 61 041 and 28 22 190.

The proportion of monomers contained in a photopolymerizable layer suitably comprising a photoinitiator within the present invention generally varies between about 10 and about 80, preferably between about 20 and about 60, percent by weight.

A great number of soluble organic polymers may be employed as binders. Examples are: polyamides, polyvinyl esters, polyvinyl acetals, polyvinyl ethers, epoxide resins, polyacrylic acid esters, polymethacrylic acid esters, polyesters, alkyd resins, polyacrylamide, polyvinyl alcohol, polyethylene oxide, polydimethyl acrylamide, polyvinyl pyrrolidone, polyvinylmethyl formamide, polyvinylmethyl acetamide, and copolymers of the monomers which form the homopolymers enumerated above.

Other suitable binders are natural substances or modified natural substances, for example, gelatin and cellulose ethers.

With particular advantage, those binders are used which are insoluble in water, but soluble or at least swellable in aqueous-alkaline solutions, since layers containing such binders can be developed with the preferably employed aqueous-alkaline developers. Binders of this type can contain for example, the following groups: —COOH, —PO$_3$H$_2$, —SO$_3$H—, —SO$_2$N—HSO$_2$— and —SO$_2$—NH—CO—.

Examples of the aforementioned binders are: maleate resins, polymers of β-methacryloyloxy-ethyl N-(p-tolyl-sulfonyl)-carbamate and copolymers of these and similar monomers with other monomers, and also styrene/maleic acid anhydride copolymers. Copolymers of alkylmethacrylate and methacrylic acid and copolymers of methacrylic acid, alkylmethacrylates and methylmethacrylate and/or styrene, acrylonitrile, and the like, which are described in German Offenlegungsschriften No. 20 64 080 and No. 23 63 806, are preferably used.

In general, the quantity of binder in a photopolymerizable layer suitably comprising a photoinitiator according to the present invention amounts to about 20 to about 90, preferably about 40 to about 80, percent by weight of the layer constituents.

Depending on their intended use and desired properties, a photopolymerizable mixture within the present invention may contain various additional substances. Examples of these are:
inhibitors to prevent thermal polymerization of the monomers,
hydrogen donors,
substances modifying the imaging properties of layers comprising the mixture,
dyes,
colored and uncolored pigments,
color formers,
indicators, and
plasticizers.

A photopolymerizable mixture of the present invention can have many applications, such as in the production of safety glass, the production of varnishes which are hardened by the action of light or other radiation, such as an electron beam, and in the manufacture of dental fillings. Such a mixture is also particularly useful as a light-sensitive copying material in the field of reproduction. Examples of possible applications in this field include: copying layers for the photomechanical production (i) of printing forms suitable for relief printing, lithographic printing, gravure printing, screen printing; (ii) of relief copies, for example, in the production of Braille books; and (iii) of single copies, tanned images, pigment images, etc. The mixtures may also be employed for the photomechanical production of etch masks, for example, for name plates, printed circuits and chemical milling.

The mixture can be used industrially for the above-mentioned applications as a liquid solution or a dispersion, such as a photoresist, which is applied by the consumer to an appropriate support, for example, for chemical milling, for the production of printed and integrated circuits, screen printing stencils, etc. The mixture can also be present as a solid light-sensitive layer on a suitable support, i.e., as a storable, presensitized copying material, such as that used for the production of printing forms. It can also be employed in the manufacture of dry resists.

It is, in general, advantageous to substantially isolate the mixtures from the influence of atmospheric oxygen during the photopolymerization. If the mixture is used in the form of thin copying layers, it is recommended to apply a suitable cover film which has a low permeability to oxygen. The cover film can be self-supporting and can be removed from the copying layer prior to development. Polyester films, for example, are suitable for this purpose. The cover film can also comprise a material which dissolves in the developer liquid or which can be removed at least from the non-hardened areas during development. Examples of materials suitable for this purpose are, inter alia, waxes, polyvinyl alcohol, polyphosphates, sugars, etc.

Layer supports which are suitable for copying materials prepared using the mixture of the present invention include, for example, aluminum, steel, zinc, copper and plastic films, such as films of polyethylene terephthalate or cellulose acetate, and screen printing supports, such as perlon gauze.

The photoinitiators according to the present invention are effective in quantities as low as about 0.05 percent of the total solids content of the composition, and an increase of this quantity beyond about 10 percent is not appropriate, as a rule. Preferably, concentrations between about 0.3 and 7 percent are used.

Furthermore, the compounds according to the present invention may be used in those radiation-sensitive compositions which, under the action of acid catalysts formed during photolysis of the initiator, undergo a change in their properties. In this connection, the cationic polymerization of systems containing vinyl ethers, N-vinyl compounds, such as N-vinyl-carbazole, or special acid-cleavable lactones are mentioned as examples, wihtout precluding the possibility that in some of these systems radical-initiated reactions may also take place. Amino plastics, such as urea/formaldehyde resins, melamine/formaldehyde resins, and other N-methylol compounds, and phenol/formaldehyde resins are also mentioned as suitable compositions which are hardened by acids. It is normal for epoxy resins to be hardened by Lewis acids or by those acids having anions which are less nucleophilic than chloride, i.e., anions of the acids formed during photolysis of the new photoinitiators. However, layers composed of epoxy resins and novolaks also harden readily upon exposure in the presence of the compounds according to the invention.

Yet another advantageous property of the new photoinitiators according to the present invention is their ability to cause color changes in dyed systems during photolysis; to induce color formation from color precursors, e.g., lueko compounds; and to cause bathochromic color shift or deepening in mixtures containing cyanine, merocyanine, or styryl dye bases. Further, in mixtures such as those disclosed in German Offenlegungsschrift No. 15 72 080, which contain a dye base, N-vinyl carbazole, and a halogenated hydrocarbon, the halogen compound tetrabromomethane may be replaced by a small percentage, i.e., about 2% of its to total amount, of at least one of the compounds of the present invention. Color changes are very desirable for certain applications, for example, in the manufacture of printing plates, because they make it possible to examine the copying result even before development of the exposed plate. The acid donors disclosed in German Offenlegungsschriften Nos. 23 31 377 and 26 41 100 are advantageously replaced by the compounds according to the present invention.

With particular advantage, the compounds according to the present invention are used in mixtures which, in addition to the compounds of the invention, contain, as an essential component, a compound containing at least one acid-cleavable C—O—C grouping. The following substances are examples of preferably used acid-cleavable compounds:

A. Compounds containing at least one orthocarboxylic acid ester group and/or carboxylic acid amideacetal group, whereby the compounds may also have a polymeric character and the above-mentioned groups may be present as connecting members in the main chain or as side groups.
B. Polymeric compounds with recurrent acetal and/or ketal groups in which preferably both α-carbon atoms of the alcohols required for forming the groups are aliphatic.

Acid-cleavable compounds of type A are described in detail as components of radiation-sensitive copying compositions in German Offenlegungsschriften Nos. 26 10 842 and 29 28 636. Copying compositions containing compounds of type B are the subject of German Patent No. 27 18 254.

Suitable acid-cleavable compounds also include, for example, the particular aryl-alkyl-acetals and -aminals disclosed in German Pat. No. 23 06 248, which are decomposed by the photolysis products of the compounds of the present invention. Other compounds of this type are enolic ethers and acyl-iminocarbonates, as disclosed by European Applications No. 6,626 and No. 6,627.

Compositions containing molecules which essentially influence the chemical and/or physical properties of the composition by their presence, and which are directly or indirectly converted into smaller molecules by the action of actinic radiation, normally show an increased solubility, tackiness or volatility in the exposed areas. These areas can be removed by suitable procedures, for example, by dissolving them away by means of a suitable developer liquid. In the case of copying materials, such systems are referred to as positive-working systems.

The novolak condensation resins which have proved suitable for many positive-working copying compositions have also been found to be suitable and advantageous additives when the compounds according to the present invention are used in compositions containing acid-cleavable compounds. These resins, in particular the more highly condensed resins containing substituted phenols as formaldehyde condensation partners, promote a strong differentation between the exposed and the unexposed areas of the layer during development. The type and quantity of the novolak resins added may vary with the intended use of the composition; novolak proportions between 30 and 90 percent by weight, especially between 55 and 85 percent by weight, based on the total solids content of the composition, are preferred.

In addition to or instead of novolaks, various other, phenol group-containing resins can be used. Additionally, concurrent use of numerous other resins is possible, with vinyl polymers, such as polyvinyl acetates, polyacrylates, polyvinyl ethers, and polyvinylpyrrolidones, which, in turn, may be modified by comonomers, being preferred. The most favorable proportion of these resins depends on practical technical requirements and on their influence on the conditions of development; normally, the proportion does not exceed 20 percent of the novolak component. For special requirements, such as flexibility, adhesion, gloss etc., minor amounts of other substances, such as polyglycols, cellulose derivatives, e.g., ethyl cellulose, surfactants, dyestuffs, finely divided pigments, and, if appropriate, UV absorbers may be added to the light-sensitive composition.

Preferably, development is effected with the aqueous-alkaline developers customary in the art, to which small proportions of organic solvents may be added. Organic solvents may also be used for developing photopolymerizable mixtures.

The supports mentioned in connection with the photopolymerizable compositions may also be used for positive-working copying materials. In addition, the silicon, silicon nitride, silicon dioxide, metal and polymer surfaces known for microelectronic processes may be used.

The quantity of compounds of the present invention, which are contained as photoinitiators in the positive-working mixtures may vary widely, depending on the substance used and the type of layer. Favorable result are obtained with proportions ranging from about 0.05 percent to about 12 percent, based on the total solids content, with proportions between 0.1 and 8 percent being preferred. In the case of layers of more than 10 μm thickness, it is recommended that a relatively small quantity of acid donor be used.

In principle, any electromagnetic radiation of a wave length up to about 550 nm is suitable for exposure. The preferred wave length range extends from 220 to 500 nm.

The large number of compounds according to this invention which have absorption maxima well within the visible range of the spectrum and absorption ranges extending beyond 500 nm make it possible to select a photoinitiator which is optimally adapted to the light source employed. In principle, sensitization is also possible. It is also advantageous to use the same photoinitiator, in accordance with the present invention, in radiation-sensitive mixtures that are exposed to radiation emitted by different sources, i.e., to radiation of different wave lengths. Many of the photoinitiators of the present invention show good results both in radiation-sensitive mixtures which are processed using automatic exposure apparatus equipped with argon-ion lasers and in copying materials which are exposed by means of metal halide doped mercury high-pressure lamps. Other suitable light sources include: tubular lamps, pulsed xenon lamps and carbon are lamps. In addition, the light-sensitive mixtures according to the present invention may be exposed in conventional projectors and enlargement apparatus, to the light of metallic-filament lamps, and by contact exposure under normal incandescent bulbs. Alternatively, other types of lasers may be used for exposure. Short-wave lasers of adequate energy output, for example, excimer lasers, krypton-ion lasers, dyestuff lasers, and helium-cadmium lasers emitting especially between 190 and 550 nm are suitable for the present invention.

As a further option, differentiation may be performed by irradiation with electron beams. Like numerous other organic materials, mixtures containing one of the compounds according to the present invention along with a compound which can be split by an acid can be thoroughly decomposed and cross-linked by exposure to electron beams, so that a negative image is formed after the unexposed areas have been removed with a solvent, or by exposure without an original, followed by development. In the case of an electron beam of lower intensity and/or higher writing speed, however, the electron beam causes a differentiation toward a higher solubility, i.e., the irradiated areas of the layer may be removed by a developer. The most favorable conditions can be easily ascertained by preliminary tests.

Preferably, the radiation-sensitive mixtures containing one of the compounds according to the present invention are used for the manufacture of printing forms, especially offset printing forms, halftone gravure printing forms, and screen printing forms, but can also be used in photoresist solutions and in dry resists.

Radiation-sensitive mixtures containing one of the compounds according to this invention are, in addition, advantageously used for the manufacture of adhesive films according to PCT Application No. 81/02261, instead of the naphthyl-bis-trichloro-methyl-s-triazines mentioned in the patent publication.

A more detailed explanation of the invention will be given by the examples which follow. In the examples, parts by weight (p.b.w.) and parts by volume (p.b.v.) bear the same relationship as grams (g) and milliliters (ml). Unless otherwise specified, percentage and volume data are to be understood as weight units.

Initially, the preparation of a number of the novel arylvinylphenyl-bis-trichloromethyl-s-triazines is described, which triazines were tested in light-sensitive mixtures according to the present invention as compounds which split off an acid and produce free radicals. These compounds were given the numbers 1 to 19 and will be referred to by these numbers in the separate examples. Some of the arylvinylphenyl carbonitriles corresponding to formula III, which were employed as starting compounds, are known from literature. The others were prepared by analogy to the method described for their simplest representative.

For the preparation of nitriles serving as starting compounds for compounds Nos. 2 to 12, 13 and 19, 4-cyano-phenylmethanephosphonic acid diethyl ester, as the P-O-activated component, was reacted with the aldehyde designated Ar-CHO in accordance with the nomenclature employed in Table I; to prepare compound 16, the reaction was performed with acetophenone. In the preparation of the starting nitrile for compound 17, the P-O-activated component was 2-cyano-phenylmethane-phosphonic acid diethyl ester. 2-chloro-4-cyano-phenylmethanephosphonic acid diethyl ester was used to synthesize the starting nitriles of compounds 13 to 15. The phosphonic acid ester was obtained in the following way: via the acid chloride and the amide, 3-chloro-4-methyl-benzoic acid was converted, by dehydration with thionyl chloride, into the 3-chloro-4-methyl-benzonitrile, which in turn was converted into the 4-bromomethyl-3-chloro-benzonitrile by reacting with N-bromo-succinimide dissolved in tetrachloro-methane; from the 4-bromomethyl-3-chlorobenzonitrile the phosphonic acid ester was obtained by reacting with triethyl phosphite.

GENERAL PROCEDURE FOR THE PREPARATION OF ARYLVINYLPHENYL CARBONITRILES BY PREPARING STILBENE-4-CARBONITRILE

A solution of 0.1 mole of benzaldehyde in 0.105 mole of 4-cyano-phenylmethanephosphonic acid diethyl ester was dropwise added, over the course of 2 hours, into a vigorously stirred mixture containing 22 g of pulverized potassium hydroxide and 200 ml of dimethyl formamide which was cooled with ice. Stirring was then continued for 1 hour with cooling and for another hour without cooling. Thereafter, the mixture was poured into 1 liter of ice water containing 52 ml of concentrated hydrochloric acid. The precipitate was removed by suction, freed from chloride ions by washing with water, dried and recrystallized from methanol.

Stilbene-4-carbonitrile having a melting point of 116°–118° C. was obtained in a quantity corresponding to 84% of the theoretical yield.

GENERAL PROCEDURE FOR THE PREPARATION OF 2-(4-ARYLVINYLPHENYL)-4, 6-BIS-TRICHLOROMETHYL-S-TRIAZINES BY PREPARING 2-(4-STYRYLPHENYL)-4,6-TRICHLOROMETHYL-S-TRIAZINE

At a temperature of 24 to 28° C., hydrogen chloride was added, up to the point of saturation, to a stirred suspension of 0.5 mole of stilbene-4-carbonitrile, 3 moles of trichloroacetonitrile and 0.06 mole of aluminum tribromide.

During this step, the solids dissolved almost completely. Then a precipitate was formed, the content of the flask took on a paste-like consistency, and the splitting off of hydrogen chloride began. For 6 hours, the mixture was kept at a temperature of 28°-30° C. by cooling; then it was allowed to sit for 24 to 48 hours at room temperature. The reaction mixture was dissolved in 1.6 liters of methylene chloride, the solution was neutralized by washing with water, and then it was dried over sodium sulfate. The solvent was thereafter distilled off under reduced pressure, the residue was dissolved in 600 ml of methylene chloride and 1,700 ml of methanol were added to the solution. 210 g (85% of theoretical) of 2-(4-styrylphenyl)-4,6-bis-trichloromethyl-s-triazine crystallized, still containing small amounts of impurities, which could be further purified by recrystallization from methylene chloride/methanol. Double melting point 160°-163° C. and 170°-173° C.

AlCl$_3$ was also a suitable catalyst. Borotrifluoride etherate was a less effective catalyst, but it yielded very pure reaction products.

The triazines listed in Table I were prepared according to the described procedure, whereby in some cases purification was performed chromatographically.

development was performed over a 1-minute period, using a developer of the following composition:

5.5 p.b.w. of sodium metasilicate ×9H$_2$O,
3.4 p.b.w. of trisodium phosphate ×12H$_2$O,
0.4 p.b.w. of sodium dihydrogen phosphate, anhydrous, and
90.7 p.b.w. of water.

A positive image of the original was obtained. A printing test conducted in an offset machine with the printing form prepared as described above was stopped after 140,000 prints, without any sign of impairment of the image quality being observed.

The copying result—measured by the number of developed continuous tone steps—that was achieved in this Example was also attained when compound No. 1 was replaced by the same quantity of one of compounds Nos. 3, 4, 5, 6, 7, 12 or 13 or of mixtures of these compounds, respectively.

If the particularly preferred initiators No. 5 and No. 20 of German Offenlegungsschrift No. 27 18 259, 2-(4-

TABLE I

| Bis-trichloromethyl-s-triazines of the general formula I with $R^2$ = H; $R^5$ = $R^6$ = H; | | | | | | | | | |
|---|---|---|---|---|---|---|---|---|---|
| Compound No. | Ar | $R^1$ | $R^3$ | $R^4$ | $R^7$ | $R^8$ | $R^9$ | λ (EtOH)/log ε | Melting point (°C.) |
| 1 | formula II | H | H | X | H | H | H | 371 nm/4.62 | 160–163 and 170–173 |
| 2 | " | H | H | X | H | H | 4-CH$_3$O | 395 nm/4.60 | 203–207 |
| 3 | " | H | H | X | H | H | 4-CH$_3$ | 381 nm/4.61 | 188–192 |
| 4 | " | H | H | X | H | H | 4-Cl | 371 nm/4.65 | 192–194 |
| 5 | " | H | H | X | 2-Cl | H | H | 362 nm/4.62 | 208–210 |
| 6 | " | H | H | X | H | 3-Cl | H | 365 nm/4.64 | 193–196 |
| 7 | " | H | H | X | H | H | 4-Br | 371 nm/4.65 | 210–211 |
| 8 | " | H | H | X | H | 3-CH$_3$O | 4-CH$_3$O | 400 nm/4.57 | 126–129 |
| 9 | " | H | H | X | H | 3,4-OCH$_2$O | | 398 nm/4.57 | 180–184 |
| 10 | " | H | H | X | H | H | 4-C$_2$H$_5$O | 397 nm/4.60 | 189–193 |
| 11 | " | H | H | X | 5-CH$_3$O | 3-CH$_3$O | 4-CH$_3$O | 389 nm/4.58 | 209–214 |
| 12 | " | H | H | X | H | H | 4-n-C$_6$H$_{13}$ | 382 nm/4.51 | 75–77 |
| 13 | " | H | Cl | X | H | H | H | 369 nm/4.56 | 215–219 |
| 14 | " | H | Cl | X | H | 3-Cl | H | 362 nm/4.58 | 191–194 |
| 15 | " | H | Cl | X | H | H | 4-CH$_3$ | 379 nm/4.56 | 210–213 |
| 16 | " | CH$_3$ | H | X | H | H | H | 355 nm/4.35 | 169–172 |
| 17 | " | H | X | H | H | H | H | 372 nm/3.80 | 107–111 |
| 18 | Naphth-1-yl | H | H | X | | | | 385 nm/4.51 | 210–214 |
| 19 | Anthrac-9-yl | H | H | X | | | | 408 nm/4.20 | 160–172 |

X = 4,6-bis-trichloromethyl-s-triazin-2-yl

EXAMPLE 1

Aluminum plates, the surfaces of which had been electrochemically roughened, anodically oxidized and pretreated with 0.1% strength aqueous solutions of polyvinylphosphonic acid, were coated with solutions comprising 6.63 p.b.w. of a cresol/formaldehyde novalak (melting range 105°-120° C., according to DIN 53181)
1.99 p.b.w. of a polymeric orthoester, prepared by condensing orthoformic acid trimethyl ester with 4-oxa-6,6-bis-hydroxymethyl octan-1-ol
0.33 p.b.w. of compound No. 1 and
0.05 p.b.w. of crystal violet base, in
30 p.b.w. of ethylene glycol monomethyl ether,
52 p.b.w. of tetrahydrofuran and
9 p.b.w. of butyl acetate, in a way such that a layer having a thickness of about 2.0 μm resulted after drying. The resulting light-sensitive layer was exposed through an original which, in addition to line and screen patterns, contained a continuous tone step wedge with 13 steps, each having an optical density increment of 0.15. Exposure was effected with a 5 kw metal halide lamp for 15 seconds, at a distance of 110 cm. After a waiting time of 10 minutes, ethoxynaphth-1-yl)- and 2-acenaphth-5-yl-4,6-bis-trichloromethyl-s-triazine, are assianged light-sensitivity factors 100 and 125, respectively, then factors between 135 and 140 are attributed to the above-mentioned photoinitiators.

EXAMPLE 2

Printing plates sized 580 mm×420 mm and consisting of aluminum foil, the surface of which had been electrochemically roughened, anodically oxidized, pretreated with polyvinylphosphonic acid, and provided with a light-sensitive layer of the following composition:

73.96 p.b.w. of the novolak of Example 1,
22.19 p.b.w. of the polyorthoester of Example 1,
3.70 p.b.w. of photoinitiator and
0.15 p.b.w. of crystal violet base were subjected to line-by-line exposure by UV radiation from an argon ion laser in a Laserite ® apparatus, whereby the number of written lines/cm was stepwise increased. The power of the laser was kept constant during this procedure. The exposed printing plate was stored at room temperature for 10 minutes, then developed with the developer of Example 1 for 60 seconds and subsequently inked with greasy ink. When a certain number of lines/cm was exceeded, the non-image areas were clear and no longer accepted ink.

The minimum energy demand required for scumfree developability of the non-image areas, which minimum depends on the photoinitiator employed, could be calculated from the laser power at the plate surface, the length of the lines, the number of lines/sec and the observed number of lines/cm. These energy values are compiled in the following table:

| Compound | Minimum energy demand (mJ/cm$^2$) |
| --- | --- |
| 1 | 6.5 |
| 3 | 7.5 |
| 4 | 6.7 |
| 5 | 5.6 |
| 6 | 6.5 |
| 7 | 6.5 |
| 12 | 7.8 |
| 13 | 5.6 |
| 14 | 7.2 |
| 16 | 7.3 |
| For comparison: | |
| 2-(4-ethoxynaphth-1-yl)-4,6-bis-trichloromethyl-s-triazine | 8.4 |
| 2-acenaphth-5-yl-4,6-bis-trichloromethyl-s-triazine | 11.2 |
| 2-(4-methoxystyryl)-4,6-bis-trichloromethyl-s-triazine | 9.2 |

The above comparison shows that the photoinitiator 2-acenaphth-5-yl-4,6-trichloromethyl-s-triazine, which is highly active when exposed to the emission of metal halide lamps, nevertheless is exceeded by the novel photoinitiators of the present invention in this application, and has a minimum energy demand in the case of laser irradiation which is 100% higher than that of compounds No. 5 and No. 13.

EXAMPLE 3

A layer of the following composition, coated onto a mechanically roughened aluminum foil from a 10% solution in methyl ethyl ketone, was exposed for 5 seconds under the same conditions as in Example 1 and developed for 45 seconds with the developer of Example 1:

76.63 p.b.w. of a phenol/formal lehyde novolak (melting range 110°-120° C., according to DIN 53181),
19.15 p.b.w. of the polyacetal of 2-ethylbutyraldehyde and triethylene glycol,
3.83 p.b.w. of compound No. 18, and
0.38 p.b.w. of crystal violet base.

A printing form carrying a positive image of the original was obtained.

The sensitivity achieved with compound No. 19 was slightly reduced.

EXAMPLE 4

The suitability as initiators of the novel bis-trichloromethyl-s-triazines of the present invention in compositions which are sensitive to electron beams is demonstrated below:

Layers comprised of
73 p.b.w. of the novolak of Example 1,
22 p.b.w. of the bis-(5-butyl-5-ethyl-1,3-dioxan-2-yl) ether of 2-butyl-2-ethyl-propane diol, and
5 p.b.w. of one of compounds No. 2, No. 9 and No. 10 were applied, in a thickness of about 1.1 μm, to mechanically roughened aluminum and irradiated with 11 kv electrons.

At a beam current of 5 μA, an irradiation time of 4 seconds was sufficient to render an area of 10 cm$^2$ soluble after developing for 60 seconds with the developer of Example 1; this corresponds to a sensitivity of the above-mentioned layers of 2 μC/cm$^2$.

EXAMPLE 5

A plate of electrolytically roughened and anodically oxidized aluminum was spin-coated with a coating solution comprised of 6.7 p.b.w. of trimethylolethane triacrylate
6.5 p.b.w. of a copolymer of methyl methacrylate and methacrylic acid, acid number 115,
0.12 p.b.w. of compound No. 1,
64.0 p.b.w. of ethyleneglycol monoethyl ether,
22.7 p.b.w. of butyl acetate and
0.3 p.b.w. of 2,4-dinitro-6-chloro-2'-acetamido-5'-methoxy-4'-(N-β-hydroxyethyl-N-β'-cyanoethylamino)-azobenzene, in a way such that a layer weight of 3 to 4 g/m$^2$ resulted after drying. Subsequently, the plate was provided with a 4 μm thick protective layer of polyvinyl alcohol (K-value 4; 12% of residual acetyl groups), exposed under a line and screen original by means of a 5 kw metal halide lamp, for 22 seconds at a distance of 110 cm, and then was developed with a 1.5% strength solution of sodium metasilicate.

A negative image of the original was obtained. A print test with an offset printing plate prepared in this way was stopped after 200,000 prints, without any impairment of the quality being observed.

EXAMPLE 6

This example describes a negative dry resist. The following coating solution, comprising 24.9 p.b.w. of a copolymer of 30 p.b.w. of methacrylic acid, 60 p.b.w. of n-hexyl-methacrylate and 10 p.b.w. of styrene,
16.1 p.b.w of the reaction product of 1 mole of 2,2,4-trimethylhexamethylene diisocyanate and 2 moles of hydroxyethyl methacrylate,
0.41 p.b.w. of triethylene glycol dimethacrylate,
0.58 p.b.w. of compound No. 5,
0.11 p.b.w. of the dyestuff used in Example 5, and
57.9 p.b.w. of methylethyl ketone, was spin-coated on a polyethylene terephthalate film, in a way such that a dry layer weight of 25 g/m$^2$ was obtained. The resulting material was laminated, in a commercially available laminator, at 120° C. onto a support of insulating material which was provided with a 35 μm thick copper layer. After exposing the material for 60 seconds through an original which, in addition to line and screen patterns included a continuous tone step wedge, by means of the light source of Example 1, and after development with an 0.8% strength sodium carbonate solution, a negative image of the line and screen pattern and steps 1 to 6 of the continuous tone step wedge remained in the form of a raised relief, step 7 being partially corroded.

The resist layer obtained was resistant to etching processes, for example, with ferric chloride, and to the influences of electroplating baths used for the production of printed circuit boards.

EXAMPLE 7

A plate of mechanically roughened aluminum was spin-coated with a solution of 4.3 p.b.w. of a phenol/formaldehyde novolak (melting range 110°–120° C., according to DIN 53181),
10.6 p.b.w. of N-vinyl carbazole,
0.24 p.b.w. of 2-(p-dimethyl-amino-styryl)-benzthiazole,
0.25 p.b.w. of one of compounds No. 15 and No. 18, and
84.6 p.b.w. of methyl ethyl ketone.

After drying, a light-sensitive layer having a thickness of about 1 to 2 μm was obtained. The plate was imagewise exposed for 7.5 seconds as described in Example 1, whereby the color of the layer changed from yellow to orange red in the image areas. By moving the plate to and fro in a developer solution comprising 0.6 p.b.w. of NaOH,
0.5 p.b.w. of $Na_2SiO_3 \times 5H_2O$,
1.0 p.b.w. of n-butanol and
97.9 p.b.w. of deionized water, the unexposed layer portions were removed within 75 seconds. The exposed areas accepted ink when the plate was wiped over with greasy ink, so that the plate prepared in this way could be used for printing on an offset machine.

With somewhat longer exposure times, it was also possible to use compounds No. 8, No. 11 and No. 17 instead of compounds No. 15 and No. 18.

EXAMPLE 8

Example 7 was repeated with the exceptions that in the coating solution the styryl dye base was replaced by the same amount of the cyanine dye base 2-[1-cyano-3-(3-ethyl-benzthiazolylidene-(2))-propen-1-yl] quinoline, that the compound No. 15 or No. 18 was replaced by the same amount of compound No. 3, and that a polyester film was coated.

When the plate was imagewise exposed for 12 seconds as in Example 1, the color of the image area changed from the initial light red to deep violet.

The non-image areas were removed by wiping the plate with the developer of Example 3. A negative image of the original was obtained.

This method can be employed for the production of color films.

EXAMPLE 9

A mechanically roughened aluminum plate was spin-coated with a layer of the following composition, from a 10% methyl ethyl ketone solution:

48.3 p.b.w. of an epoxy resin (of epichlorohydrin and bisphenol A, epoxy equivalent weight 182–194),
48.3 p.b.w. of the novolak of Example 1,
2.9 p.b.w. of compound No. 4, and
0.5 p.b.w. of crystal violet.

A negative image of the original, in which the non-image areas were free of scum, was produced by imagewise exposing the plate for 45 seconds as described in Example 1 and then developing it for 40 seconds with the developer of Example 7.

If the epoxy resin is replaced by the same amount of the above stated novolak, a negative image becomes briefly visible during development, but the resistance of the layer to the developer is so poor that the entire layer is dissolved from the support within 30 seconds.

EXAMPLE 10

Thick layers of a positive working photoresist were prepared in the following way:
A solution comprising
60 p.b.w. of butanone,
80 p.b.w. of the novolak according to Example 1,
8.58 p.b.w. of a polyacetal of 2-ethyl hexanal and pentane-1,5-diol,
0.12 p.b.w. of compound No. 7, and
1.3 p.b.w. of polyvinyl methyl ether
was applied, by means of a wire bar No. 40, to the cleaned copper surface of the laminate material of Example 6. The plate was stored for 12 hours at room temperature, so that most of the solvent evaporated. It was then post-dried for 15 minutes at 70° C. by means of infrared radiation.

The 70 μm thick resist layer thus obtained was exposed for 60 seconds through a line original by means of the light source used in Example 1 and could then be developed within 40 seconds by spray development with an 0.8% strength aqueous sodium hydroxide solution.

EXAMPLE 11

A solution comprising
23.3 p.b.w. of the novolak according to Example 1,
6.9 p.b.w. of the bis-orthoester according to Example 4, and
1.0 p.b.w. of compound No. 1, in
6.9 p.b.w. of xylene,
6.9 p.b.w. of butyl acetate and
55.0 p.b.w. of 2-ethoxy-ethyl acetate
was spin-coated, at 4,000 rpm, onto a silicon disk which was provided with a 1.0 μm thick oxide layer and which had a diameter of 7.6 cm. After 30 minutes of drying at 90° C. in a circulating air drying cabinet, the resulting resist layer had a thickness of 1.15 μm. The coated silicon disk was exposed through a mask in a contact exposure apparatus, using a mercury high pressure lamp. 5.6 mJ/cm² were sufficient to dissolve away the exposed areas of the resist layer within 90 seconds, by means of the developer used in Example 1.

What is claimed is:

1. A light-sensitive mixture comprising (a) a bistrichloromethyl-s-triazine and (b) a compound which is capable of reacting with the photoreaction product of said triazine (a) in such a way that a product is formed that has a light absorption or solubility in developer which is different from that of
(b), said triazine (a) having the formula

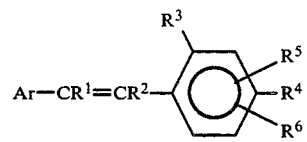

wherein
$R^1$ and R are each a hydrogen atom or a lower alkyl group,
$R^3$ and $R^4$ are different from one another and each is a hydrogen atom or a 4,6-bis-trichloromethyl-s-triazin-z-yl group
$R^5$ and $R^6$ are identical or different and each is a hydrogen atom, a halogen atom, an alkyl group having 1 to 3 carbon atoms, or a methoxy group, and Ar is (i) a mononuclear group having a formula,

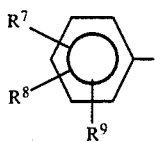

wherein $R^7$, $R^8$ and $R^9$ are identical or different and each is a hydrogen atom; a halogen atom; an unsubstituted alkyl group or an alkyl group substituted by halogen, carbocyclic aryl or carbocyclic aryloxy; such that any two of $R^7$ through $R^9$ can be connected together to form an ortho-fused 5- or 6-membered ring wherein one or two of the ring carbons can be replaced by an O- or a S-atom; a cycloalkyl group; an alkenyl group; an aryl group; or an aryloxy group, the total number of carbon atoms for $R^7$, $R^8$ and $R^9$ being 12 or (ii) a carbocyclic binuclear or trinuclear group which is unsubstituted or substituted by halogen, an alkyl group having 1 to 3 carbon atoms, an alkoxy group having 1 to 4 atoms, or an alkoxyalkyl group having 3 to 6 carbon atoms.

2. A light-sensitive mixture as claimed in claim 1, wherein said compound (b) is an ethylenically unsaturated compound which is capable of undergoing a polymerization reaction initiated by free radicals.

3. A light-sensitive mixture as claimed in claim 1, wherein said compound (b) contains at least one acid-cleavable C—O—C—bond.

4. A light-sensitive mixture as claimed in Claim 1, wherein said compound (b) is capable of undergoing acid-induced cationic polymerization.

5. A light-sensitive mixture as claimed in claim 1, wherein said compound (b) is capable of being cross-linked by an acid.

6. A light-sensitive mixture as claimed in claim 1, wherein said compound (b) has a color which is changeable by the action of an acid.

7. A light-sensitive mixture as claimed in claim 1, wherein said triazine (a) is present in an amount between about 0.05 and about 10% by weight, relative to non-volatile constituents contained in said mixture.

8. A light-sensitive mixture as claimed in claim 1, further comprising a water-insoluble polymeric binder.

9. A light-sensitive mixture as claimed in claim 8, wherein said binder is soluble in aqueous-alkaline solutions.

* * * * *